(12) United States Patent
Xia et al.

(10) Patent No.: US 11,125,633 B2
(45) Date of Patent: Sep. 21, 2021

(54) STRAIN SENSING COMPOSITIONS

(71) Applicant: The Johns Hopkins University, Baltimore, MD (US)

(72) Inventors: Zhiyong Xia, Rockville, MD (US); Vanessa D. Alphonse, Silver Spring, MD (US); Evan P. Lloyd, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/533,406

(22) Filed: Aug. 6, 2019

(65) Prior Publication Data

US 2020/0191668 A1 Jun. 18, 2020

Related U.S. Application Data

(60) Provisional application No. 62/781,148, filed on Dec. 18, 2018.

(51) Int. Cl.
*G01L 1/24* (2006.01)
*C07D 491/20* (2006.01)
*C07D 491/107* (2006.01)

(52) U.S. Cl.
CPC .......... *G01L 1/241* (2013.01); *C07D 491/107* (2013.01); *C07D 491/20* (2013.01)

(58) Field of Classification Search
CPC .... G01L 1/241; C07D 491/107; C07D 491/20
USPC ........................................................ 385/13
See application file for complete search history.

(56) References Cited

U.S. PATENT DOCUMENTS

| | | | | |
|---|---|---|---|---|
| 5,271,073 A * | 12/1993 | Hui | ...................... | G01N 21/7703 385/12 |
| 2006/0042396 A1* | 3/2006 | Qing | ................... | G01M 5/0066 73/786 |
| 2013/0264287 A1* | 10/2013 | Zhang | ..................... | C08G 81/02 210/639 |
| 2014/0013864 A1* | 1/2014 | Hickenboth | ......... | C09D 175/04 73/862.624 |
| 2016/0009845 A1* | 1/2016 | Gordon | ................... | C08C 19/20 525/94 |
| 2017/0172854 A1* | 6/2017 | Clarkson | ................... | C08F 2/48 |
| 2019/0118486 A1* | 4/2019 | Compton | ............. | B29C 64/153 |
| 2019/0151502 A1* | 5/2019 | Brosig | .................... | A61L 31/08 |

* cited by examiner

*Primary Examiner* — Jerry M Blevins
(74) *Attorney, Agent, or Firm* — Sung T. Kim

(57) ABSTRACT

Strain sensing compositions including a polymeric matrix material and a mechanophore component distributed throughout the polymeric material and covalently bonded to the polymeric material are provided. The mechanophore component undergoes a visible color change and the strain sensing composition exhibits a continuous three-dimensional (3D) spatial strain distribution including at least one color gradient upon direct or indirect impact by an object. Methods of forming strain sensing compositions are also provided. Methods of evaluating a strain distribution associated with an impact of a surrogate material comprising a mechanophore component are also provided.

19 Claims, 16 Drawing Sheets

STRAIN SENSING COMPOSITIONS

CROSS-REFERENCE TO RELATED APPLICATIONS

This application claims the benefit of U.S. Provisional Application No. 62/781,148 filed on Dec. 18, 2018, the entire contents of which are hereby incorporated herein by reference.

TECHNICAL FIELD

Embodiments of the invention relate generally to strain sensing compositions (e.g., gels, elastomers, coatings) including a polymeric matrix material and a mechanophore component distributed throughout and covalently bonded to the polymeric matrix material, in which the mechanophore component undergoes a visible color change and the strain sensing composition exhibits a continuous three-dimensional (3D) spatial strain distribution including at least one color gradient upon direct or indirect impact by an object.

BACKGROUND

High speed and/or high strain rate impact events can lead to different kinds of damage to the human body. Common high speed and/or high strain rate impact events include, for example, behind helmet blunt trauma (BHBT), traumatic brain injury (TBI), and blast or impact induced human tissue damage. Among the different types of organs involved in the damage, brain damage is particularly concerning due to the irreversible nature of nerve cells involved. Currently, there are no readily-deployable methods to directly measure, for example, intracranial brain strain and strain distribution during ballistic or similar events.

Strains of soft materials at high rates can be characterized using several technologies including strain gauges and two-dimensional digital image correlation (2D-DIC) during high-speed tensile test, split Hopkinson pressure bar test, and high-speed X-ray with lead tracers pre-embedded into a test specimen. These existing technologies suffer from a number of limitations when used for high rate testing. For example, the attachment of the strain gauges onto the specimen surface often alters the local stress field of the soft material resulting in inaccurate strain measurement. Split Hopkinson pressure bar test requires the establishment of a uniform stress/strain field through the entire length of the specimen. However, due to the low wave speed in soft materials, this is not always feasible resulting in poor data quality. 2D-DIC uses high speed cameras for capturing the surface features during the high rate process for strain calculation, but the interpolation function used for computing the strains can have a large effect on the bias errors of the matching that may lead to inaccurate measurement. When 2D-DIC is used for soft materials, marking inks are often needed due to the lack of surface features and the inks need to be compatible with the specimen surface, which is not always possible. Lastly, high-speed X-ray requires very complex instrumentation and complicated pre-test sample tracer mounting for bulk strain measurement. Most importantly, none of these existing technologies offers any direct measurements of the 3D spatial strain distribution inside the specimen during the impact event.

BRIEF SUMMARY

Certain embodiments according to the invention provide strain sensing compositions that may include a polymeric matrix material and a mechanophore component distributed throughout the polymeric matrix material and covalently bonded to the polymeric matrix material. In accordance with certain embodiments of the invention, the mechanophore component undergoes a visible color change and the strain sensing composition exhibits a continuous 3D spatial strain distribution including at least one color gradient upon direct or indirect impact by an object.

In another aspect, embodiments of the present invention provide a method of forming a strain sensing composition that may comprise covalently bonding a polymeric matrix material and a mechanophore component to form a strain sensing composition in the form of a bulk surrogate material, and configuring at least a portion of the bulk surrogate material into a shape of an anatomical organ. In accordance with certain embodiments of the invention, the mechanophore component undergoes a visible color change and the strain sensing composition exhibits a continuous 3D spatial strain distribution including at least one color gradient upon direct or indirect impact by an object.

In another aspect, embodiments of the present invention provide a method of evaluating a strain distribution associated with an impact of a surrogate material that may comprise subjecting the surrogate material to a direct or indirect impact, wherein the impact causes the mechanophore component to undergo a visible color change and the surrogate material exhibits a continuous 3D spatial strain distribution including at least one color gradient. In accordance with certain embodiments of the invention, the method may also comprise evaluating the continuous 3D spatial strain distribution exhibited by the surrogate material.

In another aspect, embodiments of the present invention provide an article comprising a substrate and a coating positioned directly or indirectly onto at least a portion of the substrate, in which the coating comprises a mechanophore component distributed throughout a matrix material.

BRIEF DESCRIPTION OF THE DRAWINGS

Embodiments of the invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout, and wherein.

DETAILED DESCRIPTION

Figure 1:
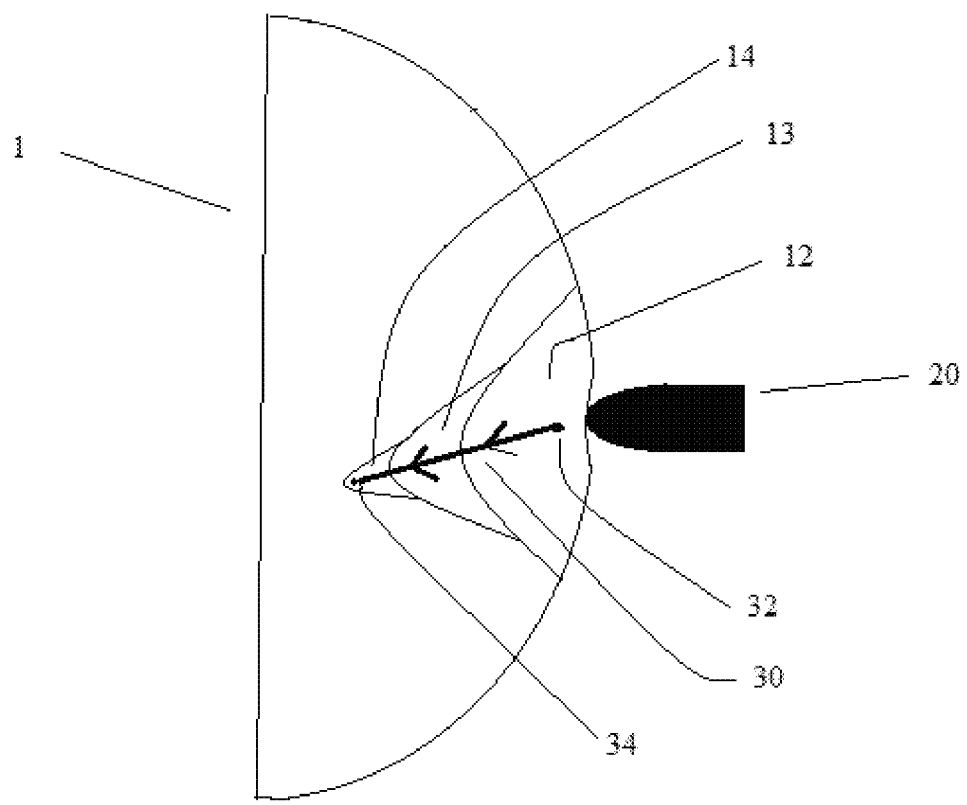
FIG. 1 illustrates a strain sensing composition impacted with a projectile and exhibiting a continuous 3D spatial strain distribution including at least one color gradient in the strain sensing composition in accordance with certain embodiments of the invention.

Embodiments of the invention now will be described more fully hereinafter with reference to the accompanying drawings, in which some, but not all embodiments of the invention are shown. Indeed, the present invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

Embodiments of the present invention relate to strain sensing compositions (e.g., gels) that can change color during impact to provide a direct measurement of the continuous 3D spatial strain distribution, including inside or on the surface of a test specimen (e.g., surrogate material in the shape of an anatomical organ) during the impact event. In accordance with certain embodiments of the invention, the strain sensing composition (e.g., a gel) may be provided in a variety of consistencies or viscosities based on, for example, an anatomical organ for which the strain sensing composition is configured to mimic. For example, the strain sensing composition may be configured in a shape and/or a consistency to mimic that of a human brain, human skin, or a human internal organ. In accordance with certain embodiments of the invention, the strain sensing composition may comprise a variety of polymeric matrix materials (e.g., natural polymeric material, synthetic polymeric material, elastomeric materials, etc.) and a mechanophore component distributed throughout the polymeric matrix material and covalently bonded to the polymeric matrix material. In this regard, as an externally-initiated strain is imparted to and propagates through the strain sensing composition, the mechanophore component can change color as a function of the intensity (e.g., magnitude) of the strain such that the strain sensing composition exhibits a continuous 3D spatial strain distribution of varying color intensities based on the relative intensity of the strain throughout the strain sensing composition. For instance, the continuous 3D spatial strain distribution of varying color intensities based on the relative intensity of the strain throughout the strain sensing composition provides both an indication of where a minimum strain threshold (e.g., a minimum strain percentage) is achieved as well as an indication of localized regions in which the strain intensity (e.g., magnitude of the strain or minimum strain percentage) is the greatest. In accordance with certain embodiments of the invention, for instance, one can visually "see" a realistic damage distribution in a surrogate material formed from a strain sensing composition by virtue of the color change and varying color intensities that provide a 3D color distribution in the strain sensing composition. For instance, the respective color changes and/or color intensities can be correlated with a particular strain level (e.g., magnitude of strain or minimum strain percentage) to provide and/or establish a 3D damage shape or distribution inside a human organ (e.g., brain). The 3D color distribution, therefore, can then help the design of, for example, helmets and other protective equipment and gear. For example, embodiments of the current invention may be used in a variety of Department of Defense and civilian applications, such as helmet design for athletic players, motorcyclists, etc. Additional examples in which embodiments of the invention may be beneficially utilized include crash test dummies for injury determination.

In accordance with certain embodiments of the invention, the strain sensing compositions may be used repeatedly for more than one use. Strain sensing compositions, in accordance with certain embodiments of the invention, may be reversible in the sense that the induced color changes due to the propagation of strain throughout the strain sensing composition begin to disappear over time and the strain sensing composition reverts back to an initial color and/or transparency prior to impact. In this regard, the strain sensing composition may be re-used for evaluation of a second impact after the strain sensing composition reverts back to the initial color and/or transparency prior to the preceding impact. The reversible nature of the strain sensing compositions, in accordance with certain embodiments of the invention, makes them ideally suited for implementing into, for example, a surrogate material or surrogate device such as a crash test dummy that will be used frequently without replacement between tests. The use of current crash test dummies does not provide the ability to quantify the area of impact. For example, the skin of crash test dummies must be covered in colored paint or powder to identify the location that impact occurred on the crash test dummy. Conversely, the reversible nature of strain sensing compositions allows for the quantification of an area of impact on the skin without adding any additional steps, such as applying paint or powder. Additionally, as a result of the reversible nature of the strain sensing compositions, there is no need to clean up after each test. Similarly, a thin coating of the strain sensing compositions may be applied to potential impact surfaces to quantify where impact occurred on the crash test dummy or the like (e.g., the inside surfaces of a vehicle). The use of current crash test dummies, if they include an abdominal structure, does not provide the ability to quantify the depth of penetration by an impact event. Integrating the strain sensing compositions into abdominal structures, such as the stomach, liver, and intestine, of crash test dummies in accordance with certain embodiments of the invention allows for measurement of the depth of penetration by blunt impacts on crash test dummies.

In accordance with certain embodiments of the invention, the strain sensing compositions also sense and/or evaluate the loading (e.g., force) applied to the strain sensing composition (e.g., a surrogate material formed from a strain sensing composition). Stress, for example, may be defined as a force applied to a certain cross-sectional area of the strain sensing composition. For instance, a stress may be considered to be the applied force or system of forces (e.g., via one or more impacts realized by the strain sensing composition) that tends to deform the strain sensing composition. From the perspective of what is happening within the strain sensing composition, stress is the internal distribution of forces within the strain sensing composition that balance and react to the loads (forces per area) applied to it. In accordance with certain embodiments of the invention, the stress distribution may or may not be uniform, depending on the nature of the loading condition (e.g., nature of the impact or impacts). When a strain sensing composition is loaded with a force (e.g., via an impact), the force produces a stress, which then causes the stain sensing composition to deform. In this regard, the strain sensing composition deforms in response to an applied stress (e.g., via one or more impacts). In accordance with certain embodiments of the invention, the continuous 3D spatial strain distribution of varying color intensities based on the relative intensity of the strain throughout the strain sensing composition is also indicative of the distribution of stress (e.g., relative locations and/or magnitude) throughout the strain sensing composition. The strain sensing compositions, in accordance with certain embodiments of the invention, therefore provide a visual measurement of both a continuous 3D spatial strain distribution and a continuous 3D spatial stress distribution. In this regard, the stain sensing compositions disclosed and described herein, may alternatively be referred to as stress and/or strain sensing compositions. For simplicity of the disclosure, the compositions disclosed and described herein are simply referred to as strain sensing compositions.

In accordance with certain embodiments of the invention, the strain sensing compositions may include a polymeric matrix material and a mechanophore component that is distributed throughout the polymeric matrix material and covalently bonded to the polymeric matrix material. In accordance with certain embodiments of the invention, the mechanophore component undergoes a visible color change and the strain sensing composition exhibits a continuous 3D spatial strain distribution, including at least one color gradient in the strain sensing composition upon direct or indirect impact by an object. For example, the strain sensing composition may be directly impacted by an external object projected (e.g., external projectile launched at the strain sensing composition) directly onto the strain sensing composition, where the external object may be, for example, a bullet, rubber bullet, construction material, athletic ball, etc. Similarly, the strain sensing composition may be directly impacted by a stationary object by moving the strain sensing composition, or article including the strain sensing composition, into the stationary object (e.g., strain sensing composition incorporated onto or within a crash test dummy that is projected into a stationary object). In accordance with certain embodiments of the invention, the strain sensing composition may be indirectly impacted by an external object (e.g., that may be stationary or projected towards the strain sensing composition), such as when the strain sensing composition is used to mimic, for example, a human head and/or brain having a test helmet or other gear covering the strain sensing composition. The external object may directly collide with the test helmet or other gear that covers the strain sensing composition, and the collision may then cause the test helmet or other gear to create a secondary impact on the strain sensing composition. As a result, the external object may have an indirect impact on the strain sensing composition. The 3D color distribution exhibited by the strain sensing composition, therefore, can be used to analyze and improve the design of, for example, helmets and other protective equipment and gear.

FIG. 1, for instance, illustrates a strain sensing composition 1 impacted with a projectile 20 and exhibiting a continuous 3D spatial strain distribution as shown by 12, 13, and 14, including at least one color gradient 30 extending from a point of most color intensity 32 to a point of least color intensity 34 in the strain sensing composition 1, in accordance with certain embodiments of the invention. The continuous 3D spatial strain distribution as shown by 12, 13, and 14 includes: (i) a first region 12 having a first color intensity generally having the greatest color intensity (e.g., brightest or darkest blue and/or purple color), (ii) a second region 13 having a second color intensity generally having an intermediate color intensity (e.g., less bright or less dark blue and/or purple color than the first color intensity), and (iii) a third region 14 having a third color intensity generally having the least color intensity (e.g., light blue and/or purple color). Although FIG. 1 illustrates each region 12, 13, and 14 as sharply defined regions, the regions may gradually transition from one region to another.

In accordance with certain embodiments of the invention, the polymeric matrix material has an average optical transmittance value of at least 50% across the visible light spectrum of approximately 380 to 740 nm, such as at least about 60%, 70%, 80%, 90%, 95%, or 99% across the visible light spectrum of approximately 380 to 740 nm. In accordance with certain embodiments of the invention, the polymeric matrix material has an average optical transmittance value of at least 50% across each wavelength within the visible light spectrum of approximately 380 to 740 nm, such as at least about 60%, 70%, 80%, 90%, 95%, or 99% across each wavelength within the visible light spectrum of approximately 380 to 740 nm. In accordance with certain embodiments of the invention, the transparency of the polymeric matrix material is not impacted by the distribution and covalent bonding of the mechanophore component while the mechanophore component is in a non-excited state (i.e., non-color forming state). In accordance with certain embodiments of the invention, the strain sensing composition has an average optical transmittance value of at least 50% across the visible light spectrum of approximately 380 to 740 nm, such as at least about 60%, 70%, 80%, 90%, 95%, or 99% across the visible light spectrum of approximately 380 to 740 nm. In accordance with certain embodiments of the invention, the strain sensing composition has an average optical transmittance value of at least 50% across each wavelength within the visible light spectrum of approximately 380 to 740 nm, such as at least about 60%, 70%, 80%, 90%, 95%, or 99% across each wavelength within the visible light spectrum of approximately 380 to 740 nm. In accordance with certain embodiments of the invention, the evaluation of the varying color intensities within the 3D color distribution exhibited by the strain sensing composition when the mechanophore component is in an excited state (e.g., color forming state due to mechanical activation, such as due to impact on the strain sensing composition) is easier upon increasing transparency of the strain sensing composition within the visible light spectrum. In this regard, for example, the resolution between the varying color intensities (e.g., subtle differences in the intensity of a blue/purple coloring may be more easily distinguished to provide better resolution of differing strain values/strain percentages throughout the strain sensing composition) within the 3D color distribution may be enhanced when the strain sensing composition is increasingly transparent.

In accordance with certain embodiments of the invention, the polymeric matrix material may comprise a natural polymer, synthetic polymer, or a combination thereof. In accordance with certain embodiments of the invention, the polymeric matrix material may comprise a silicone. In accordance with certain embodiments of the invention, the silicone may comprise a polydimethylsiloxane (PDMS) elastomer, such as a hydride, acrylamide, hydroxyl, amine, or vinyl terminated polysiloxane elastomer. Depending on the final application, the silicone elastomer can have a Shore A hardness ranging from 10 to 90 or a Shore 00 hardness of 20-100. In accordance with certain embodiments of the invention, for example, the silicone elastomer can have a Shore A hardness from at least any of the following: 10, 15, 20, 25, 30, 35, 40, 45, and 50 and/or at most about any of the following: 90, 85, 80, 75, 70, 65, 60, 55, and 50. In accordance with certain embodiments of the invention, for example, the silicone elastomer can have a Shore 00 hardness from at least any of the following: 20, 30, 40, 50, and 60 and/or at most about any of the following: 100, 90, 80, 70, 60, and 50. In accordance with certain embodiments of the invention, the polymeric matrix material comprises a silicone-based hydrogel or a cellulose-based hydrogel. The polymeric material, in accordance with certain embodiments of the invention, may comprise a thermoplastic elastomer, such as styrenic block copolymers including Poly (styrene-ethylene-butylene-styrene) SEBS, Poly (styrene-ethylene-propylene-styrene) SEPS, Poly (styrene-butadiene-styrene) (SBS), and/or Poly (styrene-isoprene-styrene) SIS, polyurethane of ether and ester type, polyurethane of aliphatic and aromatic type. In accordance with certain embodiments of the invention, the polymeric matrix material comprises an acrylic based polymer such as poly(methacrylate) (PMA), poly(hydroxy ethyl methacrylate) (poly-HEMA), and poly (ethyl acrylate) ((PEA), and poly(butyl methacrylate) (PBMA).

In accordance with certain embodiments of the invention, the mechanophore component comprises one or more compounds that may covalently bond to the polymeric matrix material and that may produce a color upon being, at least, mechanically excited or activated. The mechanophore component, in accordance with certain embodiments of the invention, may undergo a visible color change such that the strain sensing composition exhibits the continuous 3D spatial strain distribution upon the strain sensing composition undergoing a strain percentage of at least about 3%, 5%, 7%, 10%, 15%, 20%, 30%, 40%, 50%, and 60%. Strain percentage as used herein may be determined by an extension or compression of the strain sensing composition divided by the original length of the strain sensing composition, which is then multiplied by 100. For example, strain percentage may be determined by Equation (1) below where $L_2$ is the extended or compressed length and $L_1$ is the original length.

$$\text{Engineering Strain} = \left(\frac{L_2 - L_1}{L_1}\right) \times 100 \qquad \text{Equation (1)}$$

In accordance with certain embodiments of the invention, the mechanophore component comprises one or more compounds that may comprises a spiropyran (SP). A SP, for instance, may covalently bond to a variety of polymeric matrix material and includes a $sp^3$ spiro carbon-oxygen (C—O) bond that may break upon mechanical stimulation/excitement to transform the SP into its color emitting merocyanin-form. After a given period of time after mechanical stimulation, the merocyanin-form transitions back to the original SP and the color associated with the merocyanin-form disappears. In accordance with certain embodiments of the invention, for instance, the strain sensing compositions comprise a reversible nature in which color may be produced or exhibited by mechanical stimulation, and the color may disappear after a given period of time without any further mechanical stimulation (e.g., the strain sensing composition may revert back to an original/pre-mechanical activation color or optical transmittance). Stated somewhat differently, the SP comprises a multi-ring structured organic molecule and once mechanically excited, the ring structure will be opened and cause the formation of, for example, a purple or blue color. Mechanism (1) below illustrates a generic and non-limiting example SP transitioning to a corresponding merocyanin-form upon mechanical stimulation (MS) and reverting back to the original SP upon mechanical relaxation (MR) over a given period of time.

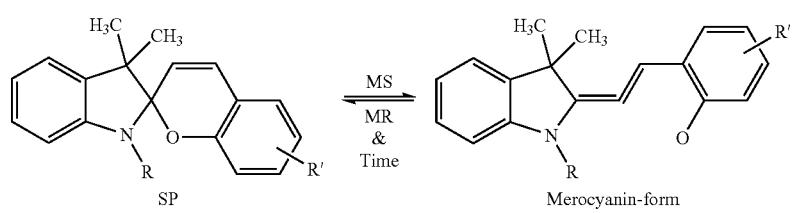

Mechanism (1)

In accordance with certain embodiments of the invention, the mechanophore component comprises a SP including an electron donating group or groups on an indole side of the SP or an electron withdrawing group or groups on a benzo-pyran side of the SP. Structure (1) shown below, illustrates a generic and non-limiting example SP noting the indole side of the SP and the benzo-pyran side of the SP.

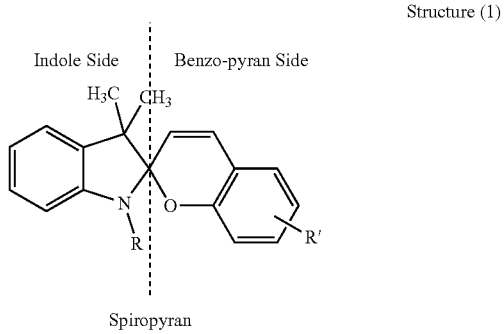

Structure (1)

In accordance with certain embodiments of the invention, the mechanophore component comprises a SP including a first functional group grafted, for example, onto a nitrogen atom of an indole side of the SP, in which the first functional group is selected to covalently bond with the polymeric matrix material. These functional groups, for example, may include hydroxyl terminated, acrylate terminated, thiol terminated, carboxylic terminated groups when used with vinyl terminated silicone, polyesters, acrylates, and other groups that can form covalent bonding the functional groups coupled to nitrogen. In accordance with certain embodiments of the invention, the SP may comprise a second functional group grafted onto a carbon atom of an indole side of the SP, in which the second functional group is selected to covalently bond with the polymeric matrix material. In accordance with certain embodiments of the invention, the SP may comprise a third functional group grafted onto an oxygen atom of a benzo-pyran/chromene side of the SP, in which the third functional group is selected to covalently bond with the polymeric matrix material. In accordance with certain embodiments of the invention, the SP may comprise a fourth functional group grafted onto a carbon atom of a benzo-pyran/chromene side of the spiropyran, in which the fourth functional group is selected to covalently bond with the polymeric material.

In accordance with certain embodiments of the invention, the functional groups grafted onto the SP that are capable of covalently bonding to the polymeric matrix or alternatively are already covalently bonded to the polymeric matrix material, (e.g., the first, second, third, and/or fourth functional groups) may be considered as anchoring locations as the covalent bonding of the SP to the polymeric matrix material effectively anchors or attaches the SP to the polymeric matrix material. In accordance with certain embodiments of the invention, the SP may comprise from about 1 to about 10 anchoring locations, such as at most about 10, 9, 8, 7, 6, 5, and 4 anchoring locations and/or at least about 1, 2, 3, and 4 anchoring locations, in which each of the anchoring locations comprises a location of covalent bonding to the polymeric matrix material. In accordance with certain embodiments of the invention, the SP includes a plurality of anchoring locations to provide an increased sensitivity (e.g., triggering of color generation at lower strain percentage thresholds and/or increased number of shades of color formation) of the SP incorporated to the polymeric matrix material. For example, increased anchoring locations between the SP and the polymeric matrix material enables a more sensitive load transfer from the polymeric matrix material to the SP for color initiation as discussed above. For example, an increased number of anchoring locations between the SP and the polymeric matrix material may enable a lower strain threshold (e.g., lower strain percentage threshold to trigger color formation) required to initial color activation of the SP in accordance with certain embodiments of the invention (e.g., increased resolution and/or sensitivity of the strain sensing composition).

In accordance with certain embodiments of the invention, the mechanophore component comprises a SP having one or more of the following non-limiting example structures:

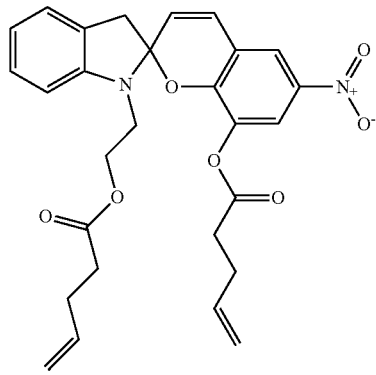

Structure 2a

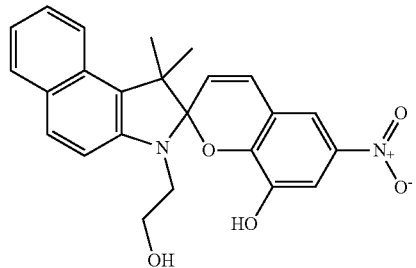

Structure 2b

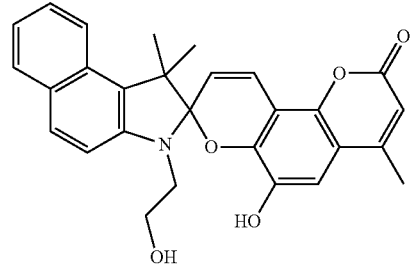

Structure 2c

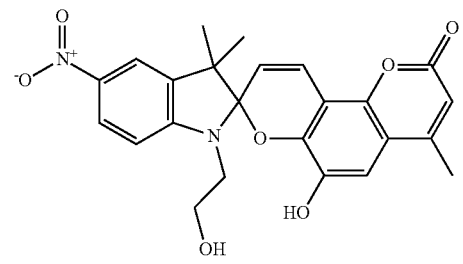

Structure 2d

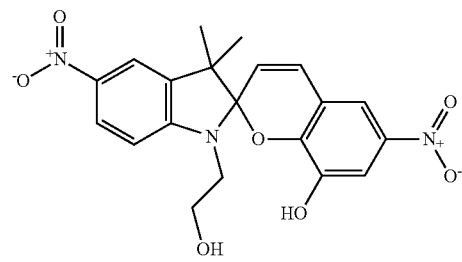

Structure 2e

Structure 2f
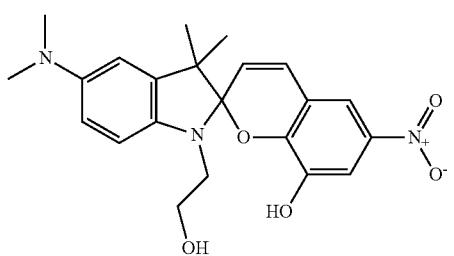

Structure 2g
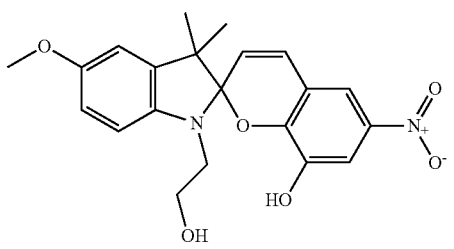

Structure 2h
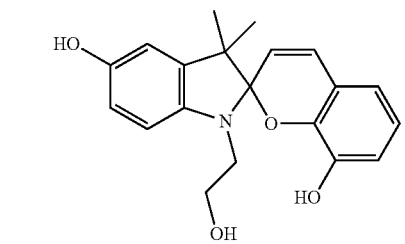

Structure 2i
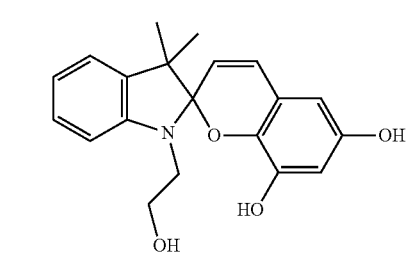

Structure 2j
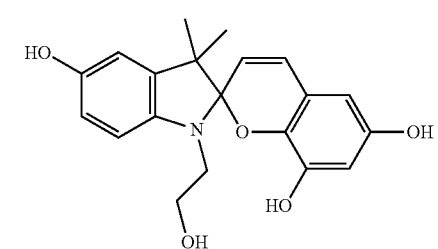

Structure 2k
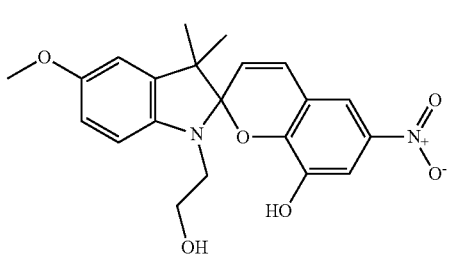

Structure 2l
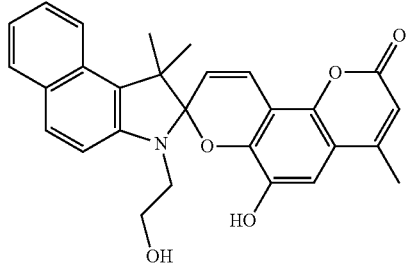

Structure 2m
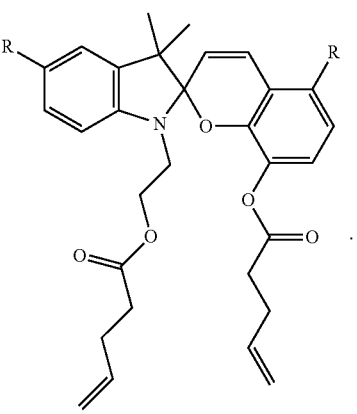

In accordance with certain embodiments of the invention, the strain sensing composition comprises from about 0.001% by weight to about 20% by weight of the mechanophore component. Stated somewhat differently, the mechanophore component may comprises from about 0.001% by weight of the strain sensing composition to about 20% by weight of the strain sensing composition, such as at most about 20, 15, 10, 8, 5, 3, 2, 1, 0.5, 0.25, and 0.1% by weight of the strain sensing composition and/or at least about 0.001, 0.01, 0.05, 0.075, 0.1, 0.25, 0.5, and 1% by weight of the strain sensing composition.

In accordance with certain embodiments of the invention, the stain sensing composition may be a surrogate material present or provided in the form or shape of an anatomical organ, such as in a form to mimic one or more of the following: a brain, skin, soft tissue organs (e.g., stomach, liver, intestine, etc.), and bone. By way of example only, the strain sensing composition may be provided in the form of a surrogate material to mimic skin (e.g., in the form of a film or gel layer) and positioned on a test dummy (e.g., a crash test dummy for vehicles). In accordance with embodiments of the invention, for instance, this would allow the crash test dummy to "show" where impact occurred due to the coloration formed due to mechanical excitement associated with a collision between the surrogate skin comprising a strain sensing composition and an external object. For example, current crash test dummies include a surrogate skin on the head, torso, pelvis, arms, and legs that do not provide any indication of where regions of contact occurred due to the collision. These current surrogate skins may be replaced by strain sensing compositions to allow for additional measurements associated with the location of contact by the external object on a crash test dummy as a result of the collision that is not currently possible.

By way of example only, the stain sensing composition may be provided in the form of a surrogate material to mimic soft tissue for a crash test dummy in which the strain sensing composition can be implemented as surrogate materials for soft tissue organ surrogates in the torso of the crash test dummy, such as a surrogate stomach, a surrogate liver, and/or a surrogate intestine comprising a stain sensing composition. For instance, such embodiments of the invention would allow the crash test dummy to "show" how deep a particular impact occurred, which cannot be measured currently.

In accordance with certain embodiments of the invention, the strain sensing composition comprises a continuous three-dimensional 3D spatial strain distribution (e.g., after an impact) including at least one color gradient including a first region having a first color intensity proximate to a location of direct or indirect impact (e.g., from a projectile) and a second region having a second color intensity that is distal to the location of direct or indirect impact and being less intense than the first color intensity. In accordance with certain embodiments of the invention, for instance, as a strain is imparted to and propagates through the strain sensing composition, the mechanophore component can change color as a function of the intensity (e.g., magnitude of the strain or strain percentage) of the strain such that the strain sensing composition exhibits a continuous 3D spatial strain distribution of varying color intensities based on the relative intensity of the strain throughout the strain sensing composition. For instance, the continuous 3D spatial strain distribution of varying color intensities based on the relative intensity of the strain throughout the strain sensing composition provides both an indication of where a minimum strain threshold is achieved as well as an indication of localized regions in which the strain intensity is the greatest. In accordance with certain embodiments of the invention, for instance, one can visually "see" a realistic damage distribution from a surrogate material formed from a strain sensing composition by virtue of the color change and varying color intensities that provide a 3D color distribution in the strain sensing composition (e.g., gel). For instance, the respective color changes and/or color intensities can be correlated with a particular strain level (e.g., magnitude of strain or strain percentage) to provide and/or establish a 3D damage shape or distribution inside a human organ (e.g., brain).

In accordance with certain embodiments of the invention, the strain sensing composition may be devoid of pressure sensors and/or electrical wiring. In accordance with certain embodiments of the invention, for example, the strain sensing compositions may provide direct indication of locations of strain and/or the magnitude of strain at different locations within the strain sensing composition without the need for burdensome pressure sensors and/or electrical wiring.

Figure 2:
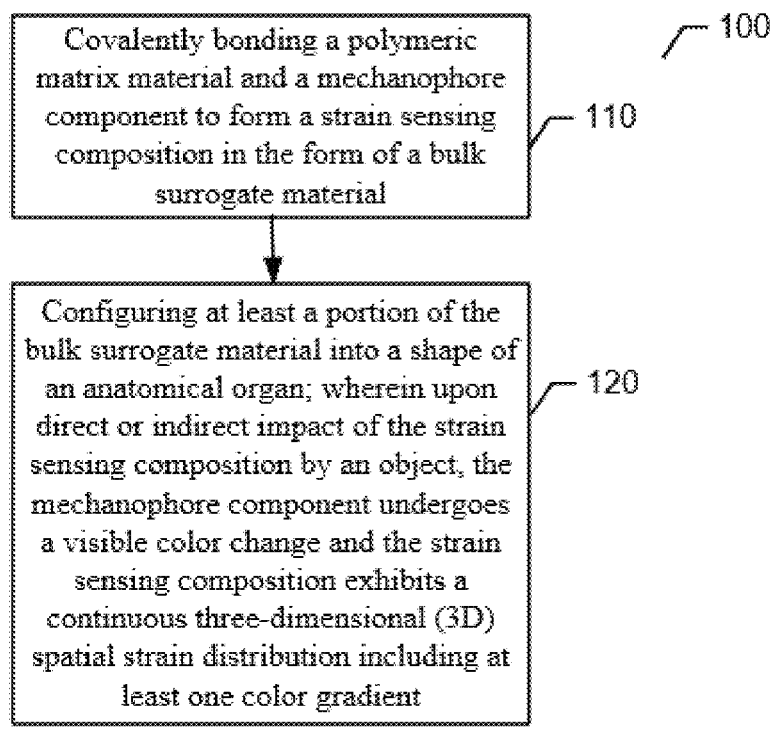
FIG. 2 illustrates a flow diagram of a method of forming a strain sensing composition in accordance with certain embodiments of the invention.

In another aspect and as illustrated by FIG. 2, embodiments of the present invention provide a method 100 of forming a strain sensing composition. In accordance with certain embodiments of the invention, the method 100 may comprise covalently bonding a polymeric matrix material and a mechanophore component to form a stain sensing composition in the form of a bulk surrogate material in operation 110, and configuring at least a portion of the bulk surrogate material into a shape of an anatomical organ in operation 120. Upon direct or indirect impact of the strain sensing composition by an object, in accordance with certain embodiments of the invention, the mechanophore component undergoes a visible color change and the strain sensing composition exhibits a continuous 3D spatial strain distribution including at least one color gradient.

In accordance with certain embodiments of the invention, for example, the method of forming a strain sensing composition may comprise configuring at least a portion of the bulk surrogate material into a shape that mimics that of an anatomical organ, such as a brain, skin, soft tissue organs (e.g., stomach, liver, intestine, etc.), bones, or any combination thereof. In accordance with certain embodiments of the invention, the configuring of the bulk surrogate material may not be particularly limited but may include, for example, 3D printing, compression molding, injection molding, reactive molding, or any combination thereof.

Figure 3:
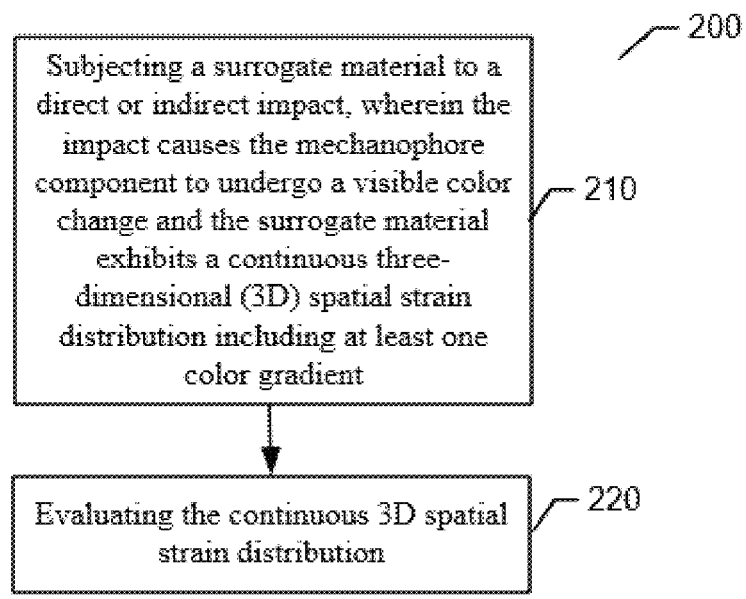
FIG. 3 illustrates a flow diagram of a method of evaluating a strain distribution associated with an impact of a surrogate material comprising a mechanophore component in accordance with certain embodiments of the invention.

In another aspect and as illustrated by FIG. 3, embodiments of the present invention provide a method 200 of evaluating a strain distribution associated with an impact of a surrogate material comprising a strain sensing composition. In accordance with certain embodiments of the invention, the method 200 of evaluating a strain distribution associated with an impact of a surrogate material may comprise subjecting the surrogate material to a direct or indirect impact, wherein the impact causes the mechanophore component to undergo a visible color change and the surrogate material exhibits a continuous 3D spatial strain distribution including at least one color gradient in operation 210. In accordance with certain embodiments of the invention, the method 200 may further comprise evaluating the continuous 3D spatial strain distribution in operation 220. For example, the continuous 3D spatial strain distribution may include a first region having a first color intensity proximate to a location of the direct or indirect impact and a second region having a second color intensity that is distal to the location of direct or indirect impact and being less intense than the first color intensity. Evaluation of the continuous 3D spatial strain distribution may comprise comparing the varying color intensities with a spectrum of standard color intensities that have been correlated to a known stress value (e.g., a known stress percentage correlated to a known color intensity). For example, the first color intensity may be correlated to a first known strain percentage and the second color intensity may be correlated to a second known strain percentage, in which the first known strain percentage is larger than the second known strain percentage. Evaluation of the continuous 3D spatial strain distribution can indicate or communicate to an evaluator (e.g., human, machine, or computer processer comparing color intensities) that the strain sensing composition experienced a greater stress (e.g., stress percentage) at the first region as compared to the second region of the spatial strain distribution.

In accordance with certain embodiments of the invention, the method of evaluating a strain distribution associated with an impact of a surrogate material comprising a strain sensing composition may include recording (e.g., via high speed camera, photograph, etc.) formation of the continuous 3D spatial strain distribution on an electronic media that can be electronically stored, distributed, and/or evaluated. For instance, recording of the formation of the continuous 3D spatial strain distribution allows for a real-time or dynamic observation and/or evaluation of the stress damage imparted to the strain sensing composition. Recording of the formation of the continuous 3D spatial strain distribution by a high speed camera!, for instance, may allow a frame-by-frame analysis of the formation of the continuous 3D spatial strain distribution, which may facilitate identification of primary and/or secondary causes of damage (e.g., initial collision with a crash test dummy providing a primary cause of damage and subsequent collision between the crash test dummy with other crash test dummies or vehicle components providing secondary causes of damage).

In accordance with certain embodiments of the invention, the method of evaluating a strain distribution associated with an impact of a surrogate material comprising a strain sensing composition may include subjecting the surrogate material to a direct or indirect impact by launching a projectile (e.g., a bullet, rubber bullet, scrap metal, construction material, athletic ball, etc.) directly or indirectly onto the surrogate material. For example, the surrogate material may be directly impacted by an external object projected directly onto the surrogate material. Additionally, the surrogate material may be indirectly impacted when the surrogate material is located behind an exterior component, such as a test helmet or other gear that covers the surrogate material for evaluation of the ability of the test helmet or gear to provide adequate protection. For example, the surrogate material may be configured to mimic, for example, a human head and/or brain having a test helmet or other gear covering the surrogate material and a projectile may be directed to collide with the test helmet or other gear that covers the strain sensing composition. Similarly, the surrogate material comprising a strain sensing composition may be directly or indirectly impacted by a stationary object by moving the surrogate material or an article including the surrogate material into a stationary object (e.g., surrogate material being incorporated onto or within a crash test dummy that is projected into a stationary object such as a wall). In accordance with certain embodiments of the invention, for example, subjecting the surrogate material to a direct or indirect impact may comprise launching the surrogate material directly or indirectly into a stationary object (e.g., wall, vehicle, etc.).

In accordance with certain embodiments of the invention, the surrogate material comprising a strain sensing composition may provide a 3D color distribution that indicates and/or communicates the protective ability of a particular test helmet or other gear. Accordingly, multiple items of protective gear may be tested and their respective protective ability may be directly compared against each other based, at least in part, on the 3D color distribution formed from each test. For example, a baseline 3D color distribution may be obtained for a baseline item protective gear (e.g., a standard helmet). As modifications are implemented to the baseline item of protective gear, a subsequent 3D color distribution for each iteration of modifications to the baseline item of protective gear may be obtained and compared to the baseline 3D color distribution. By comparison of the baseline (3D color distribution with the subsequent 3D color distributions, embodiments in accordance with the invention provide for methods of evaluating the design and manufacturing of protective gear to ensure that modifications to protective gear actually improve the protective features of the protective gear or at least do not sacrifice their protective ability.

In accordance with certain embodiments of the invention, the method of evaluating a strain distribution associated with an impact of a surrogate material comprising a strain sensing composition may comprise allowing the mechanophore component to revert back to an original color and/or transparency until the continuous 3D spatial strain distribution is no longer visible. In accordance with certain embodiments of the invention, the continuous 3D spatial strain distribution is no longer visible from about 5 minutes to about 120 minutes after impact, such as after at least any of the following: 5, 10, 15, 20, 25, 30, and 45 minutes and/or and at most any of the following: 120, 100, 90, 75, 60, 45, and 30 minutes. In accordance with certain embodiments of the invention, the method of evaluating a strain distribution associated with an impact of a surrogate material comprising a strain sensing composition may further comprise subjecting the surrogate material to a second direct or indirect impact. In accordance with certain embodiments of the invention, for instance, a single surrogate material comprising a strain sensing composition may be subjected to numerous impacts for evaluation (e.g., at least 2, 5, 10, 25, 50, 75, or 100 impacts).

In accordance with certain embodiments of the invention, the surrogate material comprising a strain sensing composition may be provided in the form and/or consistency of a brain, a head, skin, soft tissue organs (e.g., stomach, liver, intestine, etc.), bones, or any combination thereof. In accordance with certain embodiments of the invention, for example, the surrogate material may be configured (e.g., shape and/or consistency) to mimic human skin and applied as a coating (e.g., film) to an outside surface of a collision test dummy. In accordance with certain embodiments of the invention, the surrogate material comprising a strain sensing composition may be provided in the form and/or consistency of a brain (e.g., human brain), in which a test helmet or other gear may optionally be placed over the surrogate material prior to subjecting the surrogate material to an impact.

In accordance with certain embodiments of the invention, subjecting the surrogate material to the direct or indirect impact comprises a ballistic impact. For example, the ballistic impact may comprise an impact velocity comprising from about 100 m/s to about 500 m/s, such as at most about 500, 475, 450, 425, 400, 375, 350, 325, 300, and 250 m/s and/or at least about 100, 150, 200, 250, and 300 m/s.

Figure 4:
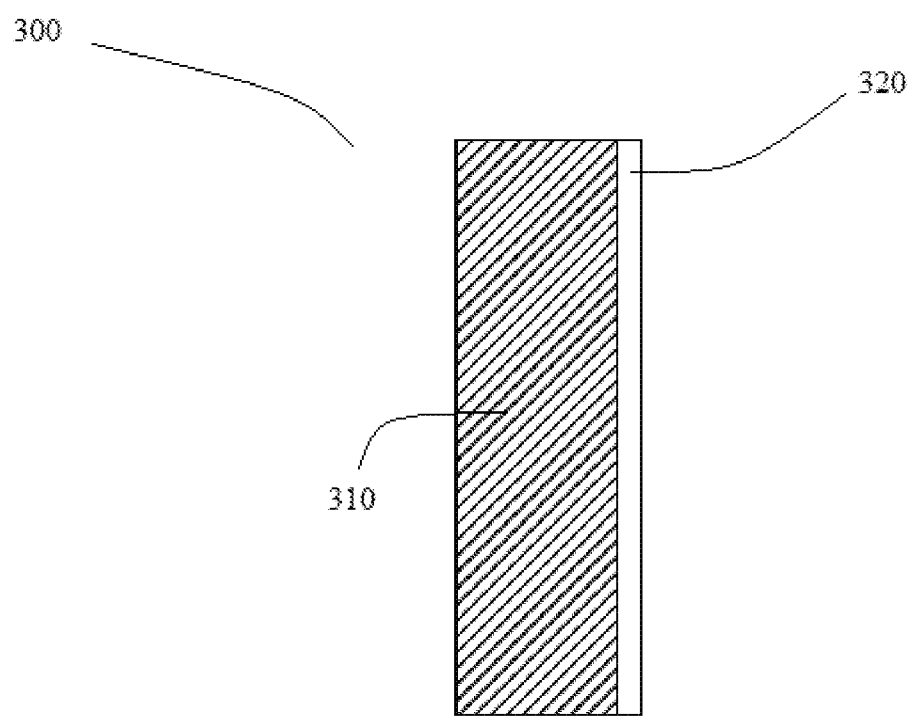
FIG. 4 illustrates a cross-sectional view of an article in accordance with certain embodiments of the invention.

In another aspect and as illustrated by FIG. 4, embodiments of the present invention provide an article 300 comprising a substrate 310 and a coating 320 positioned directly or indirectly onto at least a portion of the substrate, in which the coating comprises a mechanophore component distributed throughout a matrix material. In accordance with certain embodiments of the invention, the matrix material comprises a film of a natural and/or synthetic material, a primer coating, or a paint coating. In accordance with certain embodiments of the invention, the substrate comprises a glass, a polycarbonate, a metal, or a polymeric material (e.g., fiber-reinforced composite). For example, the substrate may comprise a component of a vehicle, such as a windshield, body panel of a vehicle, contact lens, or a mammalian organ. In accordance with certain embodiments of the invention, the mechanophore component is covalently bonded to the matrix material. The mechanophore component, in accordance with certain embodiments of the invention, may comprise a SP as described and disclosed herein. In accordance with certain embodiments of the invention, the mechanophore component may comprise from about 0.001% by weight of the strain sensing composition to about 50% by weight of the coating, such as at most about 50, 40, 30, 25, 20, 15, 10, 8, 5, 3, 2, 1, 0.5, 0.25, and 0.1% by weight of the strain sensing composition and/or at least about 0.001, 0.01, 0.05, 0.075, 0.1, 0.25, 0.5, 1, 5, 10, 15, 20, and 25% by weight of the coating.

In accordance with certain embodiments of the invention, the article 300 may comprise a vehicle and the coating 320 comprising the mechanophore component distributed throughout the matrix material may beneficially form a color distribution upon an impact and/or stress fracture formed and/or forming at a location on the vehicle. In this regard, structurally weak and/or damaged portions of a vehicle may be readily identifiable upon the visual observation of the color distribution formed on the vehicle.

In accordance with certain embodiments of the invention, the mechanophore component (e.g., a SP as disclosed herein) also has photochromic properties in which the mechanophore component produces a change of color in the coating by incident radiation (e.g., exposure to ultraviolet light). For example, the coating may exhibit a color change in response to exposure to light due to reversible photochromic properties of the mechanophore component (e.g., a SP as disclosed herein). In accordance with certain embodiments of the invention, the mechanophore component transitions from an original color or state (e.g., an initial non-color exhibiting state) to a second, color exhibiting state upon exposure to radiation between, for example, 250 nm to 700 nm (e.g., 250 nm and 380 nm). In accordance with certain embodiments of the invention, once exposure to radiation has stopped the mechanophore component begins to transition back to the original color or state (e.g., an initial non-color exhibiting state). In accordance with certain embodiments of the invention, the photochromic properties of the mechanophore component may be leveraged in certain applications, such as coatings on windshields, eye shields, eye glasses, and contact lenses. For instance, transparent or semi-transparent articles (e.g., windshields, eye shields, eye glasses, contact lenses, etc.) including a coating including a mechanophore component, in accordance with certain embodiments of the invention, may transition to a light-blocking and/or a light-reflecting state upon exposure to radiation (e.g., ultraviolet light) to provide protection from the radiation (e.g., ultraviolet light) due to the color formation associated with the mechanophore component. Upon cessation of exposure to the radiation (e.g., ultraviolet light), the mechanophore component transitions back to an original color or state (e.g., an initial non-color exhibiting state).

In accordance with certain embodiments of the invention, the article may comprise a medical device implanted into a mammal to monitor, for example, pressure formation on a given organ and/or to indicate the growth of a tumor. For example, the substrate 310 may comprise a mesh or support structure that may be sutured in place within a mammal while the coating 320 comprising the mechanophore component may be supported thereon. The matrix material, for example, may comprise a natural polymeric material (to which the mechanophore component may be covalently bonded) that may be safely introduced into a mammal, such as natural polymers that make up much of a mammal's extracellular matrix. For example, the matrix material may comprise a collagen, elastin, or fibrinogen. In accordance with certain embodiments of the invention, detection of color formation due to activation of the mechanophore component may indicate and/or communicate that a particular region is being subjected to an undesirable pressure (e.g., stress due to the growth of a tumor or enlargement of an organ).

EXAMPLES

The present disclosure is further illustrated by the following examples, which in no way should be construed as being limiting. That is, the specific features described in the following examples are merely illustrative and not limiting.

As discussed above, by introducing anchoring locations (e.g., pulling locations) on one or both the indole and/or benzo-pyran sides of the S—C—O junction of an SP, the SP can be covalently bound to the polymeric matrix material, effectively coupling mechanical stress in the polymeric matrix material to the C—O bond. For these examples, poly(dimethyl siloxane) (PDMS) was selected for its ease on tunability in mechanical properties and optical clarity. Alkene groups incorporated on both sides of the spiro junction allow easy covalent incorporation into commercially available PDMS kits, which form networks using platinum catalyzed hydrosilylation. Since the transition between SP and the merocyanin-form (MC) is reversible, the color change in these stain sensing compositions is fully recoverable and the stain sensing compositions can thus be used multiple times for impact sensing.

These examples demonstrate the application of the SP mechanophores for sensing the impact strains in a PDMS elastomer, referred to as SP-PDMS hereafter. These examples also demonstrate the use of SP mechanophore as a cost effective, passive strain sensor for measuring 3D spatial strains under impact conditions, which may ultimately be used as a surrogate material (e.g., a brain surrogate for quantifying brain strain for traumatic brain injury (TBI), an injury that is responsible for 30% of all injury death in the Unites States alone.)

1. Experimental 1.1. Quasi-Static Tensile Test and Color Analysis

Quasi-static tensile testing was performed according to ASTM D412 with a die C geometry using a screw-driven MTS 30G at an extension rate of 0.36 mm/s at room temperature and the strain was measured via a strain gauge. During the tensile testing, a charge coupled device camera (Logitech Brio, Newark, Calif., USA) was used to observe color change. The color of the quasi-static samples after stretching was deconvoluted into R, G, B values. Since the color of the specimen after deformation is primarily blue, a 'blueness' parameter was adopted for quantifying the color of each sample. The 'blueness' (B %) was computed by averaging the B value over the entire R, G, B scale, that is, B %=B/(R+G+B).

1.2. SP Synthesis

3',3'-dimethyl-6-nitro-1'-(2-(pent-4-enoyloxy)ethyl)spiro[chromene-2,2'-indolin]-8-yl pent-4-enoate or spiropyran was synthesized according to known methods with the following modifications made to the amounts of reagents and purification methods. To an oven dried round bottom flask, 1'-(2-hydroxyethyl)-3',3'-dimethyl-6-nitrospiro[chromene-2,2'-indolin]-8-ol (3.0 g, 8.14 mmol, 1 equiv) and 4-dimethylaminopyridine (0.099 g, 0.814 mmol, 0.1 equiv.) were dissolved in dry dichloromethane (40 mL). The dark green suspension was stirred and 4-pentenoic anhydride (3.20 mL, 17.51 mmol, 2.15 equiv) was added in 3 separate aliquots, with 15 min between each addition. The reaction was stirred overnight, resulting in a magenta-purple solution. The mixture was extracted with concentrated sodium bicarbonate solution (1×75 mL), 1 N hydrochloric acid (1×75 mL), water (2×75 mL) and brine (1×75 mL) before drying over sodium sulfate. The crude product was collected from rotary evaporation as crude purple oil. Boiling petroleum ether (300 mL) was poured into the oil, then the solution was hot filtered and let stand to develop yellow-green crystalline SP (3.21 g, 74%). Characterization matched the compound reported in literature.

1.3. SP-PDMS Elastomer Block Synthesis

An elastomer block was made with PDMS from Sylgard®184 from Dow Corning and 0.25 wt % SP mechanophore. SP was first dissolved in para-xylene at a concentration of 75 mg/mL followed by incorporating in the Sylgard®184 mixtures with different ratios of base (i.e., PDMS) to curing agent (SP) by volume (10:1, 20:1 and 30:1). The mixture was then degassed under vacuum for about 30 min until all gas bubbles were removed. The corresponding tensile and impact samples were then made by curing the mixers at ambient temperature for 48 h to ensure adequate formation of the network structure.

1.4. High Rate Impact Test and Finite Element Analysis

The high rate impact was performed using an in-house air cannon test system for achieving impact loading condition. During the test, a domed cylindrical projectile (outer diameter 40 mm, length 52.5 mm, dome radius of curvature 20 mm and mass 29 g) made of 3D printed glass filled nylon was inserted into the air cannon barrel. The air pressure was then regulated to achieve a projectile impact speed from 80-110 m/s. Finite element analysis (FEA) used for predicting stress/strain distributions was performed using LS-Dyna based on parameters obtained from Mooney-Rivlin analysis of the quasi-static tensile test data. A Lagrangian formulation and an Euler forward time stepping algorithm were employed, with the time step size automatically chosen for numerical stability.

2. Results

As discussed, the color change of SP relies on the rupture of the Spiro C—O bond and the transformation of SP into longer conjugated MC. The latter absorbs strongly at a wavelength of 550-600 nm and leads to formation of purple color in SP-PDMS. Since MC is metastable, once the mechanical stimulus is removed, the sprio C—O bond will be reformed reversing MC into the original SP. The latter leads to the disappearance of the purple color and thus allows for multiple uses. In these examples, alkene functionalized SP was used to couple with a vinyl terminated PDMS (i.e., Sylgard®184 from Dow Corning). The hydrosilylation reaction between Si—H and alkene groups lead to the formation of covalent bonding between SP and PDMS, resulting in the transfer of the load and thus color change upon impact.

Figure 5A:
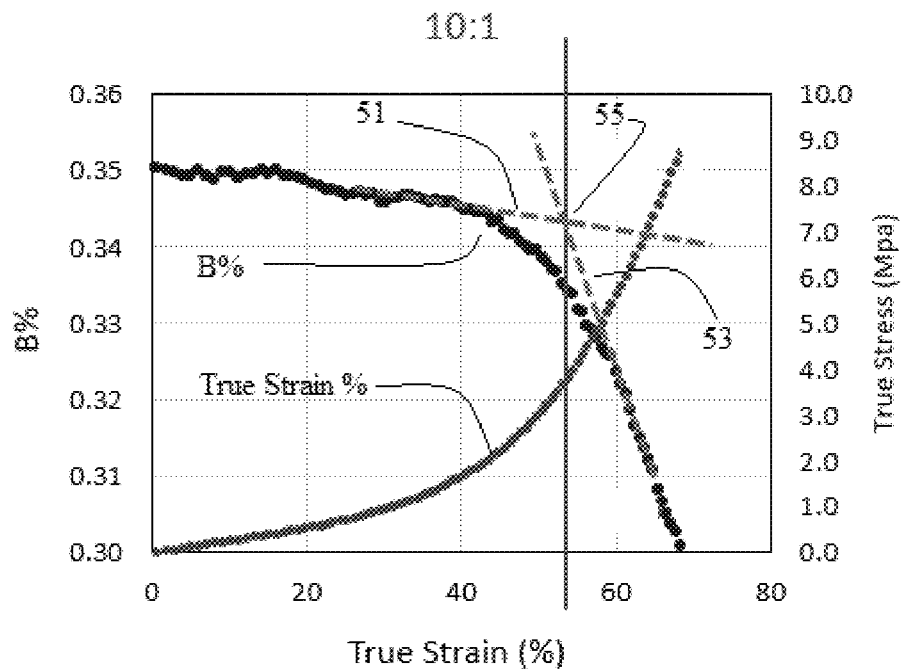
FIG. 5A shows the results at a strain rate of 0.014 s-1 for the 10:1 mixing ratio (silicone:spiropyran) in accordance with certain embodiments of the invention.
Figure 5B:
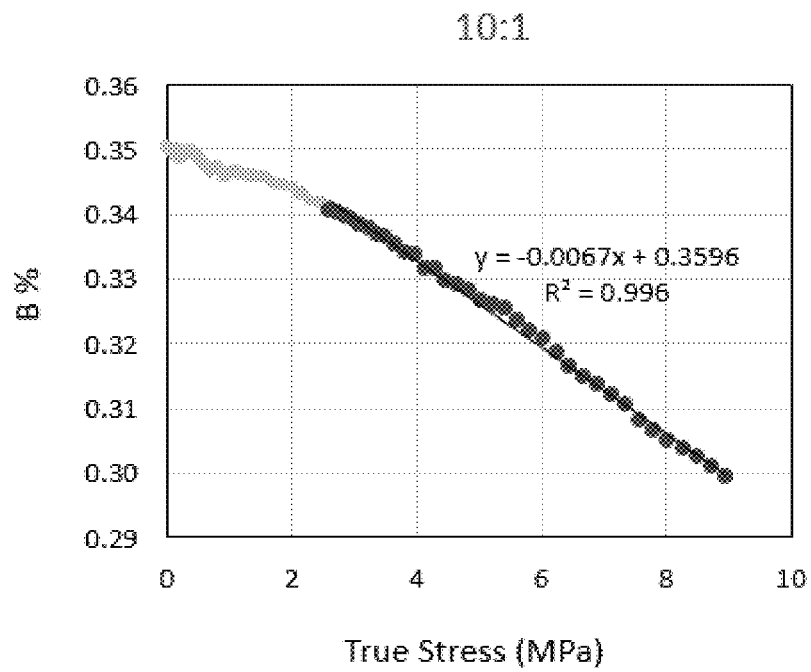
FIG. 5B shows the 'blueness' (B %) as function of True Stress for the 10:1 mixing ratio (silicone:spiropyran) of FIG. 5A.
Figure 5C:
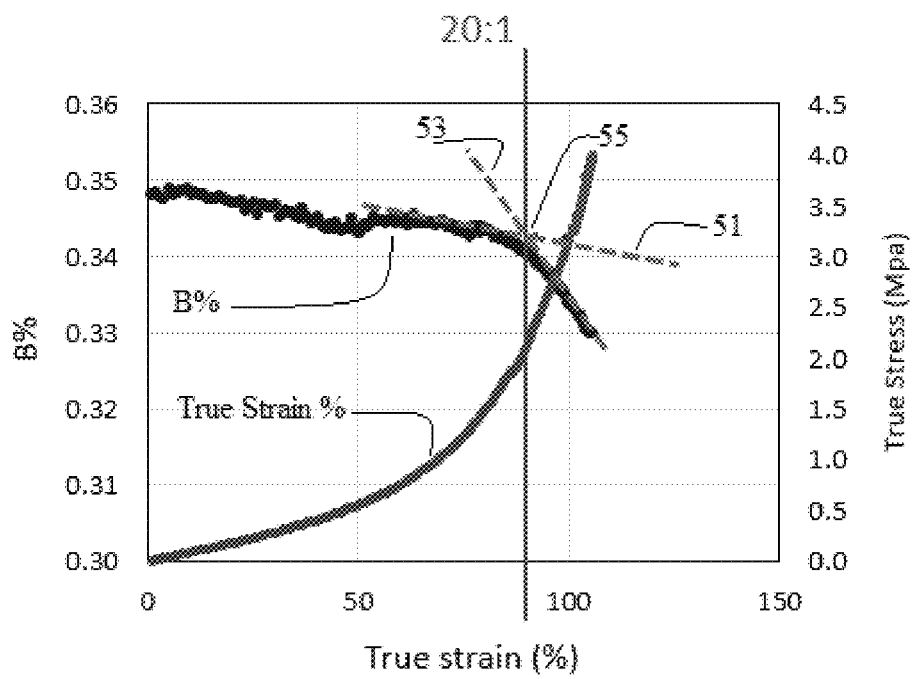
FIG. 5C shows the results at a strain rate of 0.014 s-1 for the 20:1 mixing ratio (silicone:spiropyran) in accordance with certain embodiments of the invention.
Figure 5D:
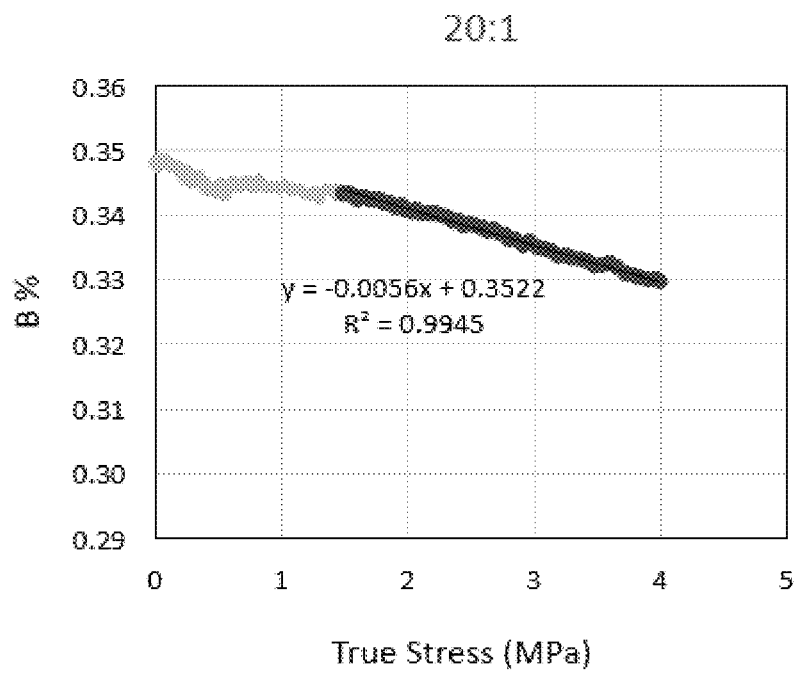
FIG. 5D shows the 'blueness' (B %) as function of True Stress for the 20:1 mixing ratio (silicone:spiropyran) of FIG. 5C.
Figure 5E:
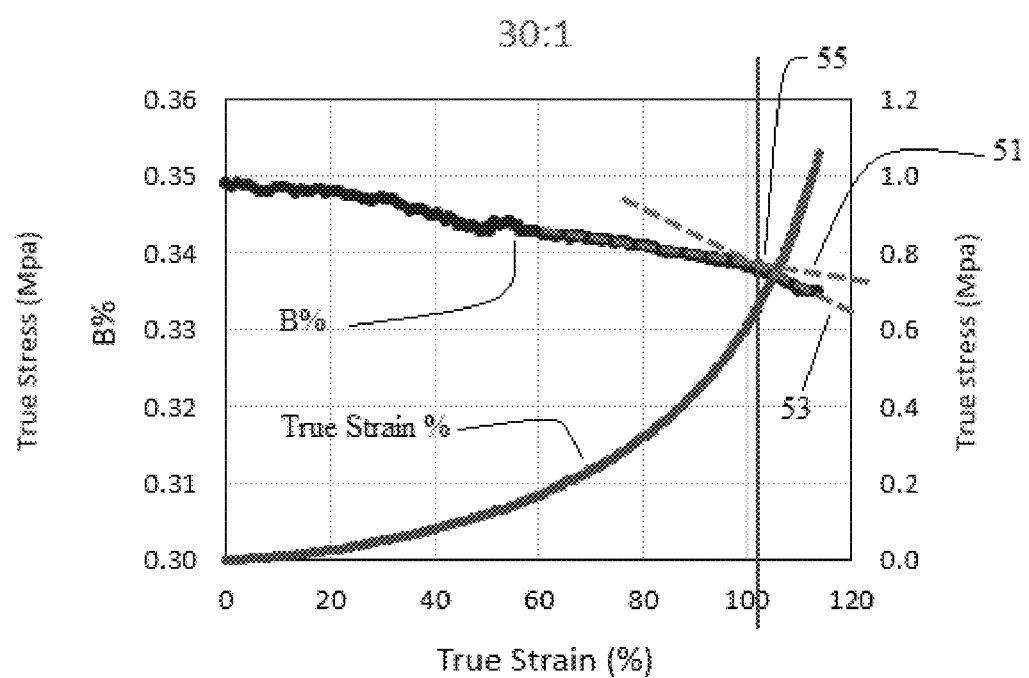
FIG. 5E shows the results at a strain rate of 0.014 s-1 for the 30:1 mixing ratio (silicone:spiropyran) in accordance with certain embodiments of the invention.
Figure 5F:
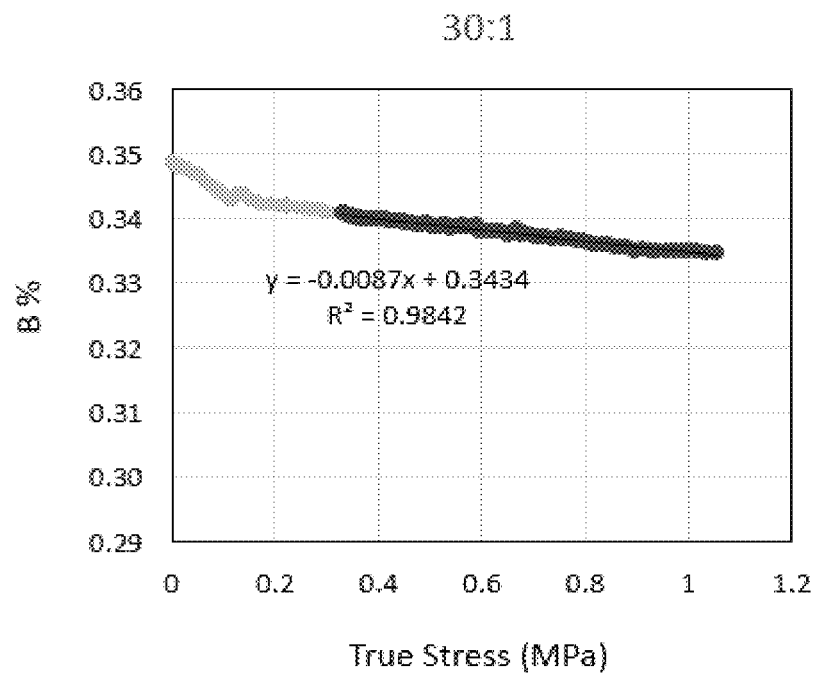
FIG. 5F shows the 'blueness' (B %) as function of True Stress for the 30:1 mixing ratio (silicone:spiropyran) of FIG. 5E.

To understand the effect of PDMS network structure on the color change of SP, two part Sylgard® 184 prepared at three different mixing ratios (i.e., PDMS:SP in the following ratios—10:1; 20:1; and 30:1) were tested under uniaxial tensile mode. FIG. 5A shows the results at a strain rate of 0.014 s-1 for the 10:1 mixing ratio. FIG. 5B shows the 'blueness' (B %) as function of True Stress for the 10:1 mixing ratio (silicone:spiropyran) of FIG. 5A. FIG. 5C shows the results at a strain rate of 0.014 s$^{-1}$ for the 20:1 mixing ratio. FIG. 5D shows the 'blueness' (B %) as function of True Stress for the 20:1 mixing ratio (silicone: spiropyran) of FIG. 5C. FIG. 5E shows the results at a strain rate of 0.014 s$^{-1}$ for the 30:1 mixing ratio. FIG. 5F shows the 'blueness' (B %) as function of True Stress for the 30:1 mixing ratio (silicone:spiropyran) of FIG. 5E. In all three samples, SP loading level was controlled at 0.25 wt. %. It can be seen that the decrease in blue (B %) initiated around the onset of the strain-hardening region. The onset point was determined by drawing lines tangent to the initial and final portions of the same curve with the interception of the drawing lines tangent to the initial and final portions of the same curve with the interception of the two lines defined as the onset point. In this regard, FIGS. 5A, 5C, and 5E illustrate a first tangent line 51, a second tangent line 53, and onset point 55. For the 10:1 mixing ratio, the onset true strain for the color change was found to be around 53%. With the increase in mixing ratio to 20:1 and 30:1, the onset true strain values for the color change increased to 92% and 102%, respectively. FIGS. 5B, 5D, and 5F each show B % values plotted against true stress which demonstrates a close to linear relationship after the onset of strain hardening.

To better characterize the PDMS network structure, the Mooney-Rivlin analysis was employed as shown in Equation (2).

$$\frac{\sigma_{emgr}}{\left(\lambda - \frac{1}{\lambda^2}\right)} = 2C_1 + 2C_2\frac{1}{\lambda} \qquad \text{Equation (2)}$$

where $\sigma_{engr}$ is engineering stress, $\lambda$ is extension ratio, $C_1$ and $C_2$ are materials constants and relate to the network crosslinking density and the deviation from ideal rubber, respectively. $C_1$ and $C_2$ can be determined by plotting the following:

$$\frac{\sigma_{emgr}}{\left(\lambda - \frac{1}{\lambda^2}\right)} \text{ versus } \frac{1}{\lambda}$$

with slope and intercept being $2C_2$ and $2C_1$, respectively. The ratio of $2C_2/C_1$ measures the looseness of the network structure. With $C_1$ and $C_2$ known, the average molecular weight between crosslinks ($M_c$) (kg/mol) and the network crosslinking density (N) (mol/m$^3$) can be further determined via Equation (3):

$$\overline{M_c} = \frac{\rho RT}{2C_1 + 2C_2} = \frac{\rho R}{\kappa N} \qquad \text{Equation (3)}$$

In the above equations, $\kappa$ is the Boltzmann constant of $1.38 \times 10^{-3}$ J/K, $\rho$ is density (g/cm$^3$), T is temperature (K) and R is the gas constant of 8.31 J/mol*K.

Figure 6:
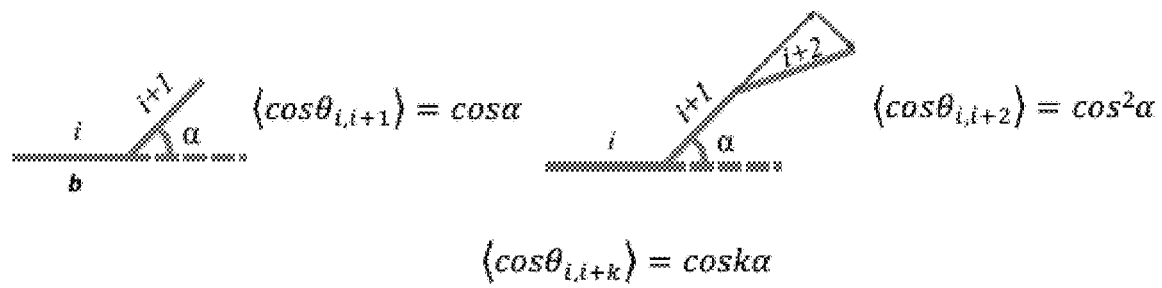
FIG. 6 shows a conceptual illustration to better understand the SP-PDMS gelation network stretchability using a fixed valence angle model.

To better understand the SP-PDMS gelation network stretchability, the mean end-to-end distance (<r>) of PDMS chains using a fixed valence angle model, as conceptually illustrated in FIG. 6 and understood in the art, was computed as follows via Equation (4).

$$\langle r^2 \rangle = nb^2 \frac{1 - \cos\alpha}{1 + \cos\alpha} \qquad \text{Equation (4)}$$

The force (f) that is required to perturb the chain dimensions can be shown according to Equation (5):

$$f = \frac{3\kappa T}{Nb^2} \langle r \rangle \qquad \text{Equation (5)}$$

where n is the number of repeat units between crosslinks, b is the Si—O bond distance of 1.63 Angstroms and a is the bond angle of 50°.

Table 1 shows the computed results based on the Mooney-Rivlin analysis at a strain rate of 0.014 s-1. It can be seen that with the increase in mixing ratio from 10:1 to 30:1, $M_c$ increased by a factor of twelve and N dropped by a factor of six indicating the formation of a looser network structures. Table 1 also shows the mean end-to-end distance (<r>) of PDMS computed using a fixed valence angle model (Equation (4)), which shows that with the increase of mixing ratio from 10:1 to 30:1, <r> increased by a factor of three.

TABLE 1

| Sylgard® 184 Mixing Ratio | C1 (kPa) | C2 (kPa) | $M_C$ (kg/mol) | N (mol/m³) | Onset True Strain for Blue Color (B %) Change | Root Mean End-to-End Distance (<r>) (Å) |
|---|---|---|---|---|---|---|
| 10:1 | 611 | 189 | 1.6 | 646 | 53% | 9.7 |
| 20:1 | 168 | 123 | 4.4 | 235 | 92% | 16.1 |
| 30:1 | 99 | 30 | 19.5 | 104 | 102% | 33.9 |

To address the effect of network structure on the color change in SP, the theoretical maximum network stretch ratio ($\lambda_t$) was calculated based on ratio between average chain contour length ($\tau$) between crosslinks and <r>. These results are summarized in Table 2, which shows that with the increase in mixing ratio, the measured extension ratio ($\lambda_m$) to $\lambda_t$ decreased. Table 2 also shows the force (f) required to perturb the chains computed based on Equation (5) decreased with the increase in <r> value. Since the color change in SP depends on the PDMS stretching induced spirocyclic C—O bond rupture, a smaller $\lambda_m/\lambda_t$ will lead to a lower stress (see last column in Table 2) being acted on the C—O bond causing less color change at a given strain. This finding is also consistent with the force calculation.

FIGS. 9A-9D show the progression of a projectile during impact. The formation of the high strain areas are evident. With the progression of the projectile, the maximum shear strain zone was pushed further into SP-PDMS block. FIGS. 9A-9D were taken during the impact process of a sample 90 and show that the formation of dark "blue" color 600 (shown as a shaded region inside the sample 90) during the impact from a projectile launched from cannon 93. Note this color is different than the purple color observed in FIGS. 8A-8D which was taken after the impact process. A detailed analysis of the high-speed impact video obtained at a frame rate of 30,000 per second showed that color change in SP-PDMS as fast as 33 μs was readily achieved during the ballistic impact event. Since the time frame of most impact events is in the

TABLE 2

| Sylgard® 184 Mix Ratio | Chain Contour Length between Crosslinks ($\tau$) (Å) | Maximum Theoretical Extension Ratio ($\lambda t = \tau/<R>$) | Measured Extension Ratio ($\lambda m$) | Observed Elongation for the Onset of Blue Color Change ($\lambda o$) | Percent Reached to Theoretical Extension Ratio ($\lambda m/\lambda t$) | Force Required to Perturb the Chain Dimensions (f) (picuNewton-pN) |
|---|---|---|---|---|---|---|
| 10:1 | 33.1 | 3.6 | 2.0 | 1.6 | 56% | 20.9 |
| 20:1 | 96.4 | 6.0 | 2.9 | 2.4 | 49% | 12.6 |
| 30:1 | 429.4 | 12.7 | 3.1 | 2.7 | 29% | 6.0 |

Figure 7:
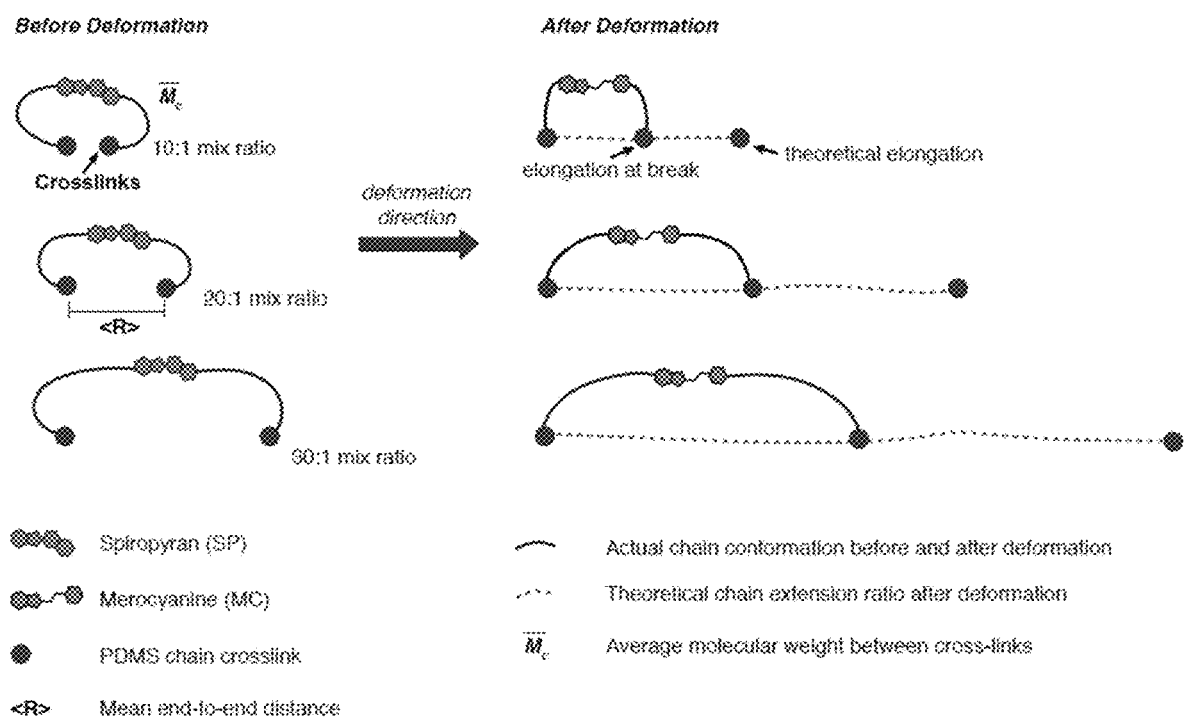
FIG. 7 is a schematic illustration of the effect of cross-linking density on the stretchability of the PDMS network as a function of the mixing ratio.

A schematic on the effect of crosslinking density on the stretchability of the PDMS network is illustrated in FIG. 7, which illustrates schematically, that the chain contour length and mean end-to-end distance where lower mixing ratios led to higher crosslinking density and thus smaller average molecular weight between crosslinks. Since high $M_c$ means long 'PDMS loop length' between crosslinks, a high theoretical network stretchability ($\lambda_t$) will ensue. At the same loading condition, the latter will compromise the effective stretching of SP and reduce the probability of transformation of SP into MC. As a result, at the same stretch ratio, the amount of the stress generated in PDMS with a higher mixing ratio will be much lower than that of a 'tighter' network structure. The latter in turn leads to higher extension for the onset of color change ($\lambda_o$) as shown in Table 2.

2.1. High Strain Rate Impact Results

Figure 8A:
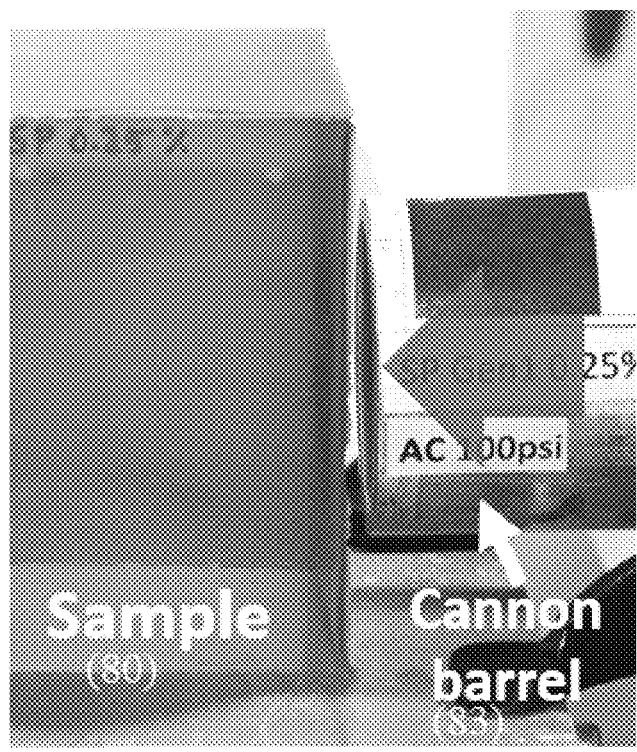
FIGS. 8A-8D show the representative color change in SP-PDMS before and after multiple impacts in accordance with certain embodiments of the invention.
Figure 8B:
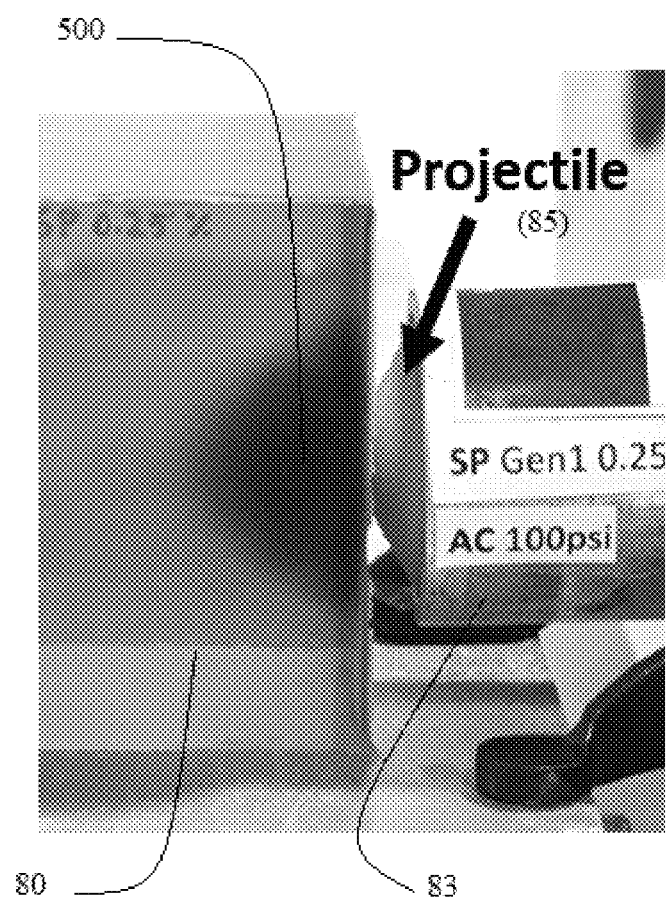
Figure 8C:
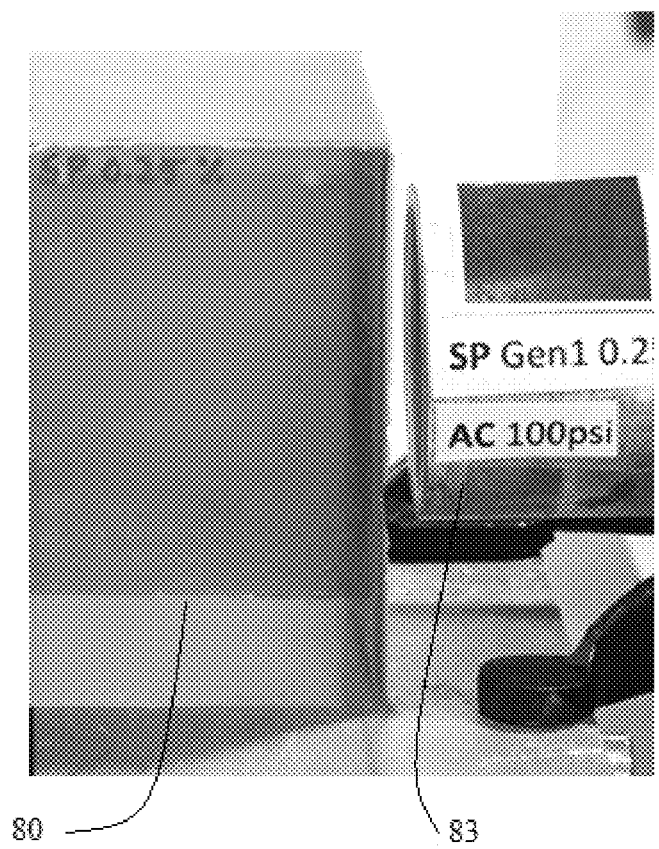
Figure 8D:
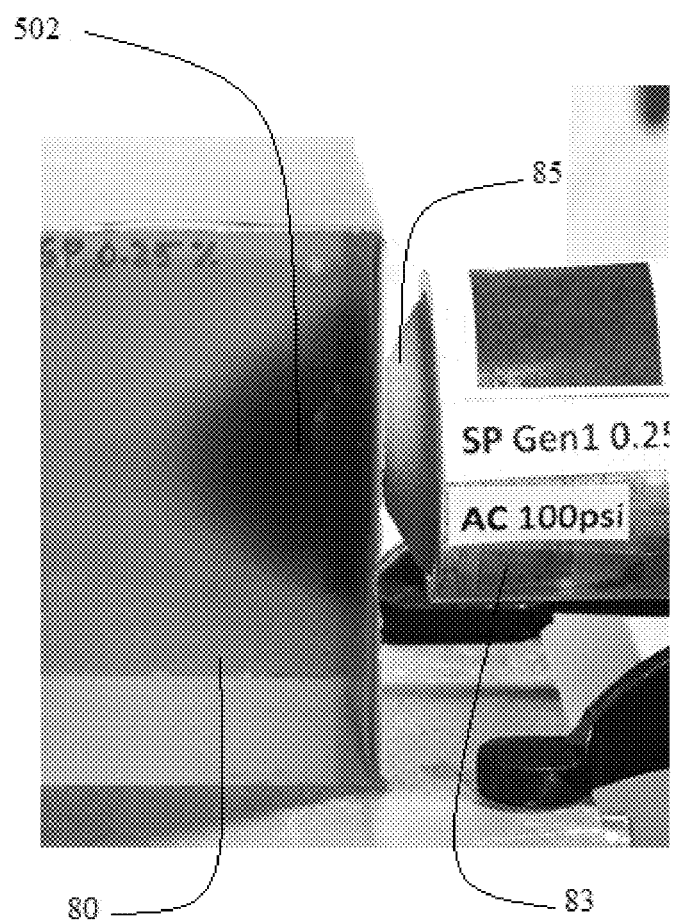
Figure 9A:
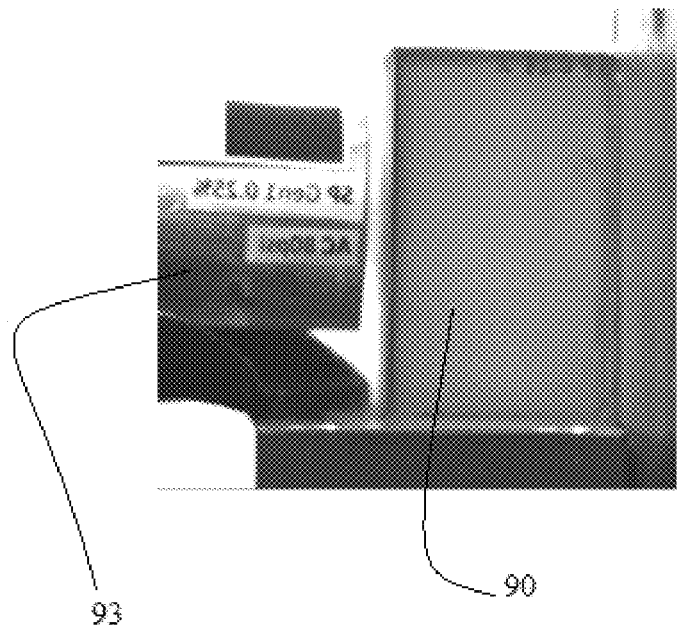
FIGS. 9A-9D are successive images taken during an impact process that show the formation of a dark color during the impact in accordance with certain embodiments of the invention.
Figure 9B:
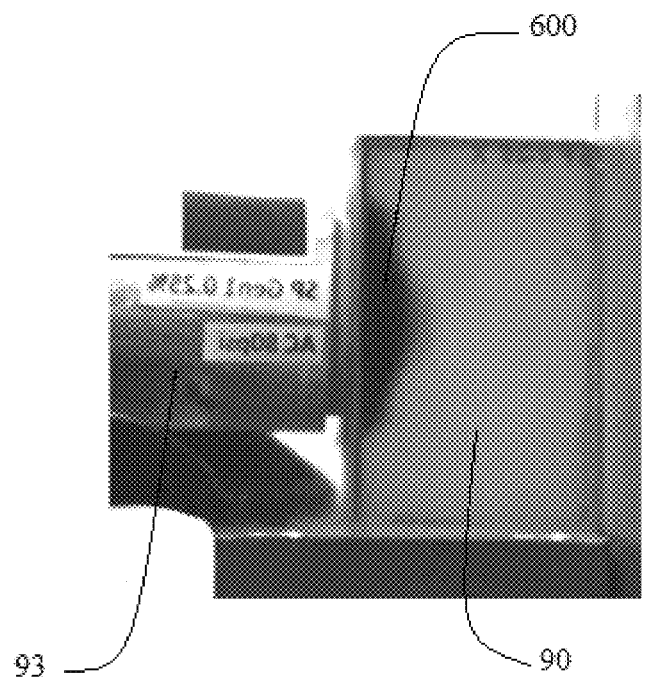
Figure 9C:
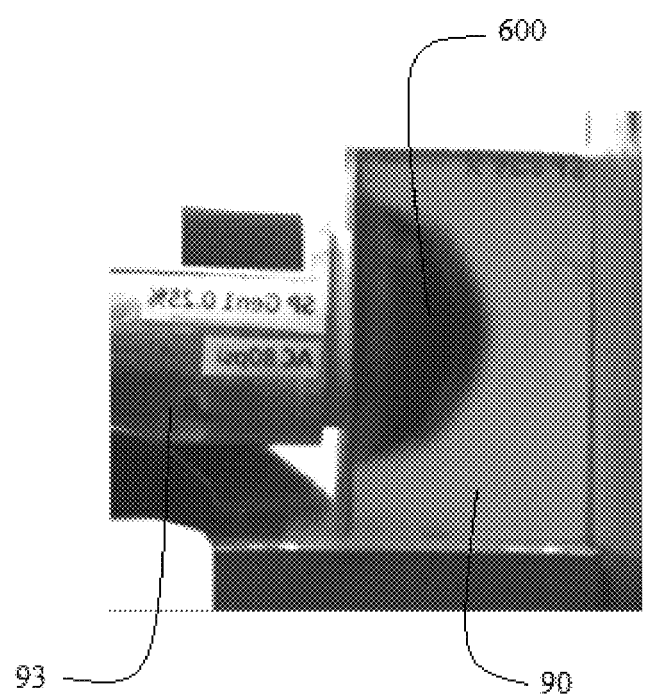
Figure 9D:
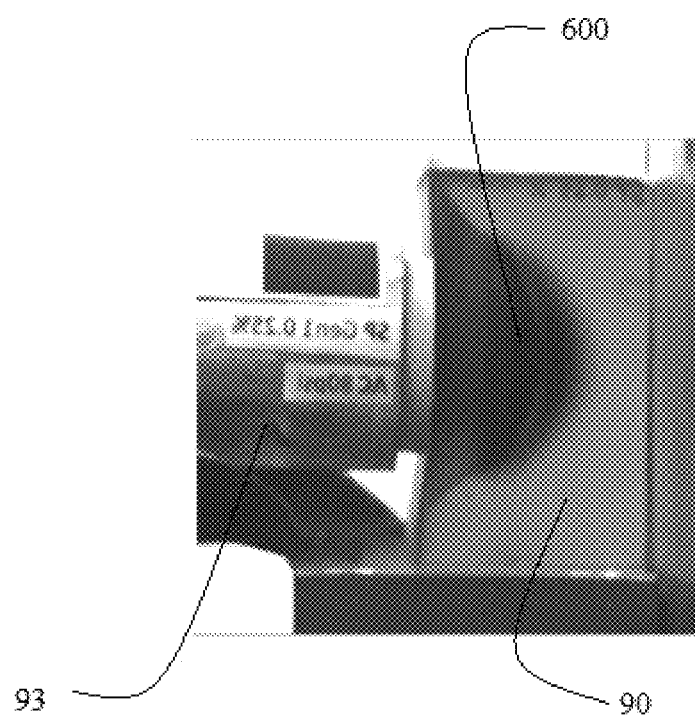

To further understand the high strain rate behavior, a SP-PDMS block (7.62 cm×7.62 cm×7.62 cm in size) with 10:1 mixing ratio was studied at impact speed ranging from 80-110 m/s. FIGS. 8A-8D show the representative color change in SP-PDMS before and after multiple impacts. FIG. 8A shows the SP-PDMS sample 80 prior to any impacts with cannon barrel 83 directed towards the SP-PDMS sample 80. Immediately after the first impact with a projectile 85, a "purple" cloud 500 (shown as a shaded region) inside the sample block 80 was formed showing the high strain contour during the impact as shown in FIG. 8B. After about 26 min, the purple color fully disappeared indicating the switching back from MC to SP as shown in FIG. 8C. A subsequent second impact had reformed the 'purple cloud' 502 demonstrating the reusability of SP-PDMS for sensing impact strains as shown in FIG. 8D.

neighborhood of microseconds, a 33 μs response time in SP-PDMS is thus fast enough for the SP to capture the impact induced damage in PDMS. Additionally, the time response SP is also affected by both the PDMS matrix viscoelastic properties and the impact rate as the load being transferred to the Spiro junction is a direct function of the combined effects of both. A closer examination of SP-PDMS block after impact showed the presence of a purple surface ring. This is because the low shear modulus of the SP-PDMS caused a very slow hear wave speed of 26 m/s. This shear wave was much slower than the bulk wave speed of 1461 m/s and prevented the relaxation of PDMS on the specimen surface during impact and led to the formation of high strain rings on the surface of SP-PDMS. This result was also confirmed by FEA.

2.2. Example Applications

These examples have demonstrated, at least, that SP-PDMS elastomer block (e.g., strain sensing composition) can be used for 'seeing' the dynamic impact strain under ballistic conditions. By examining the color distribution in the SP-PDMS, an overall 3D spatial strain contour can be established. Since the color change can 'remember' the highest strain regions for the same impact duration, this technology can be used to visualize the highest strain levels in a test sample. This latter finding, if used for traumatic brain injury (TBI) application, for example, can be used for sensing the regions susceptible to brain injury whereas none of the existing technologies can provide this output. In TBI, it has been shown that the most effective strategy in reducing brain injury is the use of impact resistant helmets. As a result, one way of adopting this technology, in accordance with certain embodiments of the invention, is to use SP-PDMS (or similar strain sensing composition) as a brain surrogate for TBI protecting helmet evaluation. For example, by comparing the SP-PDMS color during impact to the relationship established between color and strain under quasi-static conditions, a continuous strain distribution in the PDMS can then be established. Since certain embodiment in accordance with the invention, do not require the use of any pressure sensors which only measure impact at discrete locations, the overall strain spatial distribution inside the brain surrogate can be obtained, allowing the visualization of impact induced brain strain in situ. A color holding time of 26 min is also desirable and can allow for post impact brain surrogate imaging and damage analysis. Finally, certain embodiments of the invention provide a new way of visualization of, for example, brain strain during high rate impact, These and other modifications and variations to embodiments of the invention may be practiced by those of ordinary skill in the art without departing from the spirit and scope of the invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

That which is claimed:

1. A strain sensing composition, comprising:
   (i) a polymeric matrix material; and
   (ii) a mechanophore component distributed throughout the polymeric matrix material and covalently bonded to the polymeric matrix material, wherein the mechanophore component comprises a spiropyran having from 3 to 10 anchoring locations including a first anchoring location defined by a third functional group grafted onto an oxygen atom of a benzo-pyran side of the spiropyran, and wherein each of the anchoring locations comprises a location of covalent bonding to the polymeric matrix material;
   wherein upon direct or indirect impact of the strain sensing composition with an object, the mechanophore component undergoes a visible color change and the strain sensing composition exhibits a continuous three-dimensional (3D) spatial strain distribution including at least one color gradient.

2. The strain sensing composition of claim 1, wherein the polymeric matrix material has an average optical transmittance value of at least 50% across the visible light spectrum of approximately 380 to 740 nm.

3. The strain sensing composition of claim 1, wherein the polymeric matrix material comprises a silicone.

4. The strain sensing composition of claim 1, wherein the spiropyran comprises (i) a first functional group grafted onto a nitrogen atom of an indole side of the spiropyran; wherein the first functional group is selected to covalently bond with the polymeric matrix material; (ii) a second functional group grafted onto a carbon atom of an indole side of the spiropyran; wherein the second functional group is selected to covalently bond with the polymeric matrix material; or (iii) both (i) and (ii).

5. The strain sensing composition of claim 1, wherein the spiropyran comprises a fourth functional group grafted onto a carbon atom of a benzo-pyran side of the spiropyran; wherein the fourth functional group is selected to covalently bond with the polymeric matrix material.

6. The strain sensing composition of claim 1, wherein the spiropyran comprises from 4 to 10 anchoring locations.

7. The strain sensing composition of claim 1, wherein the mechanophore component comprises a spiropyran including (i) an electron donating group on an indole side of the spiropyran, (ii) an electron withdrawing group on a benzo-pyran side of the spiropyran, or (iii) both (i) and (ii).

8. The strain sensing composition of claim 1, wherein the mechanophore component comprises from about 0.001% by weight of the strain sensing composition to about 20% by weight of the strain sensing composition.

9. The strain sensing composition of claim 1, wherein the strain sensing composition is a surrogate material provided in the geometric form of a brain, skin, soft tissue organ, bone, or any combinations thereof.

10. The strain sensing composition of claim 1, wherein the continuous 3D spatial strain distribution includes a first region having a first color intensity proximate to a location of direct or indirect impact of the strain sensing composition by the object, and a second region having a second color intensity that is distal to the location of direct or indirect impact of the strain sensing composition by the object, wherein the second color intensity is less intense than the first color intensity.

11. The strain sensing composition of claim 1, wherein the strain sensing composition exhibits the continuous 3D spatial strain distribution upon the strain sensing composition undergoing a minimum strain percentage of about 10%.

12. The strain sensing composition of claim 1, wherein the strain sensing composition exhibits the continuous 3D spatial strain distribution upon the strain sensing composition undergoing a minimum strain percentage of about 3%.

13. A method of forming a strain sensing composition, comprising:
    (i) covalently bonding a polymeric matrix material and a mechanophore component to form a strain sensing composition in the form of a bulk surrogate material, wherein the mechanophore component comprises a spiropyran having from 3 to 10 anchoring locations including a first anchoring location defined by a third functional group grafted onto an oxygen atom of a benzo-pyran side of the spiropyran, and wherein each of the anchoring locations comprises a location of covalent bonding to the polymeric matrix material; and
    (ii) configuring at least a portion of the bulk surrogate material into a shape of an anatomical organ; wherein upon direct or indirect impact of the strain sensing composition by an object, the mechanophore component undergoes a visible color change and the strain sensing composition exhibits a continuous three-dimensional (3D) spatial strain distribution including at least one color gradient.

14. The method of claim 13, wherein configuring at least a portion of the bulk surrogate material into a shape of an anatomical organ comprises 3D printing, compression molding, injection molding, reactive molding, or any combinations thereof.

15. A method of evaluating a strain distribution associated with an impact of a surrogate material comprising a mechanophore component, the method comprising:
    (i) subjecting the surrogate material to a direct or indirect impact, wherein the impact causes the mechanophore component to undergo a visible color change and the surrogate material exhibits a continuous three-dimensional (3D) spatial strain distribution including at least one color gradient, wherein subjecting the surrogate material to a direct or indirect impact comprises launching a projectile directly or indirectly into the surrogate material or launching the surrogate material directly or indirectly into a stationary object; and (ii) evaluating the continuous 3D spatial strain distribution exhibited by the surrogate material.

16. The method of claim 15, wherein the continuous 3D spatial strain distribution includes a first region having a first color intensity proximate to a location of the direct or indirect impact, and a second region having a second color intensity that is distal to the location of direct or indirect impact and is less intense than the first color intensity; wherein the first color intensity is correlated to a first known strain percentage and the second color intensity is correlated to a second known strain percentage, and the first known strain percentage is larger than the second known strain percentage.

17. The method of claim 15, further comprising digitally recording the surrogate material during the direct or indirect impact; wherein a dynamic evaluation of the continuous 3D spatial strain distribution is captured on a digital recording media.

18. The method of claim 15, wherein the surrogate material comprises at least a portion of a crash test dummy.

19. The method of claim 15, wherein the method further comprises covering at least a portion of the surrogate material with a test helmet and subjecting the surrogate material to an indirect impact by launching the projectile directly into the test helmet.

* * * * *